(12) United States Patent
Richardson et al.

(10) Patent No.: US 9,999,464 B2
(45) Date of Patent: Jun. 19, 2018

(54) DEVICE AND METHODS FOR RENAL NERVE MODULATION MONITORING

(71) Applicant: Boston Scientific Scimed, Inc., Maple Grove, MN (US)

(72) Inventors: Leonard B. Richardson, Brooklyn Park, MN (US); Scott R. Smith, Chaska, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days. days.

(21) Appl. No.: 15/664,120

(22) Filed: Jul. 31, 2017

(65) Prior Publication Data
US 2017/0325881 A1 Nov. 16, 2017

Related U.S. Application Data

(60) Continuation of application No. 14/837,562, filed on Aug. 27, 2015, now Pat. No. 9,743,982, which is a division of application No. 13/678,306, filed on Nov. 15, 2012, now Pat. No. 9,119,600.

(60) Provisional application No. 61/560,026, filed on Nov. 15, 2011.

(51) Int. Cl.
| | | |
|---|---|---|
| *A61B 18/18* | (2006.01) |
| *A61B 18/14* | (2006.01) |
| *A61B 90/00* | (2016.01) |
| *A61B 18/16* | (2006.01) |
| A61B 18/00 | (2006.01) |
| A61B 18/20 | (2006.01) |
| A61B 17/32 | (2006.01) |

(52) U.S. Cl.
CPC .......... *A61B 18/1492* (2013.01); *A61B 18/16* (2013.01); *A61B 90/00* (2016.02); *A61B 17/320068* (2013.01); *A61B 18/1815* (2013.01); *A61B 18/20* (2013.01); *A61B 90/39* (2016.02); *A61B 2018/00029* (2013.01); *A61B 2018/00285* (2013.01); *A61B 2018/00434* (2013.01); *A61B 2018/00446* (2013.01); *A61B 2018/00511* (2013.01); *A61B 2018/00547* (2013.01); *A61B 2018/00577* (2013.01); *A61B 2018/00815* (2013.01); *A61B 2018/00821* (2013.01); *A61B 2018/00875* (2013.01); *A61B 2018/167* (2013.01); *F04C 2270/0421* (2013.01)

(58) Field of Classification Search
USPC .......................................................... 606/41
See application file for complete search history.

(56) References Cited

U.S. PATENT DOCUMENTS

| | | | | |
|---|---|---|---|---|
| 2004/0172075 A1* | 9/2004 | Shafer | ................ | A61N 1/36114 607/9 |
| 2007/0135875 A1* | 6/2007 | Demarais | ................ | A61F 7/123 607/96 |
| 2010/0168561 A1* | 7/2010 | Anderson | .......... | A61B 17/3403 600/424 |

* cited by examiner

*Primary Examiner* — Nicole F Johnson (57) ABSTRACT

Systems and methods for monitoring and performing tissue modulation are disclosed. An example system may include an elongate shaft having a distal end region and a proximal end and having at least one modulation element and one sensing electrode disposed adjacent to the distal end region. The sensing electrode may be used to determine and monitor changes in tissue adjacent to the modulation element.

20 Claims, 7 Drawing Sheets

DEVICE AND METHODS FOR RENAL NERVE MODULATION MONITORING

CROSS-REFERENCE TO RELATED APPLICATIONS

This application is a continuation of U.S. application Ser. No. 14/837,562, filed Aug. 27, 2015, which is a divisional of U.S. application Ser. No. 13/678,306, filed Nov. 15, 2012, now U.S. Pat. No. 9,119,600, which claims priority under 35 U.S.C. § 119 to U.S. Provisional Application Ser. No. 61/560,026, filed Nov. 15, 2011, the entirety of which is incorporated herein by reference.

TECHNICAL FIELD

The present invention relates to methods and apparatuses for nerve modulation techniques such as ablation of nerve tissue or other destructive modulation technique through the walls of blood vessels and monitoring thereof.

BACKGROUND

Certain treatments require the temporary or permanent interruption or modification of select nerve function. One example treatment is renal nerve ablation which is sometimes used to treat hypertension and other conditions related to hypertension and congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many nerves (and nervous tissue such as brain tissue), including renal nerves, run along the walls of or in close proximity to blood vessels and thus can be accessed intravascularly through the walls of the blood vessels. In some instances, it may be desirable to ablate perivascular renal nerves using a radio frequency (RF) electrode in an off-wall configuration. However, the electrode and/or temperature sensors associated with the device may not be able to detect tissue changes in the target region because the electrode is not in contact with the wall. Sensing electrodes may allow the use of impedance measuring to monitor tissue changes. It is therefore desirable to provide for alternative systems and methods for intravascular nerve modulation.

SUMMARY

The disclosure is directed to several alternative designs, materials and methods of manufacturing medical device structures and assemblies for performing and monitoring tissue changes.

Accordingly, one illustrative embodiment is a system for nerve modulation that may include an elongate shaft having a proximal end region and a distal end region. An ablation electrode and a first sensing electrode may be disposed on the elongate shaft adjacent to distal end region. The system may further include a ground pad. The ablation electrode, sensing electrode, and ground pad may be electrically connected to a control unit.

Another illustrative embodiment is a method for detecting tissue changes during tissue modulation. A tissue modulation system including an elongate shaft having a proximal end region and a distal end region may be provided. The modulation system may further include a first electrode disposed adjacent the distal end region and a second electrode disposed adjacent to the distal end region and spaced a distance from the first electrode. The modulation system may be advanced through a lumen such that the distal end region is adjacent to a target region. Voltage may be applied to the modulation system to impart a current between the first and second electrodes and an impedance of the target region may be calculated from the current. Voltage may be applied to at least one of the first or second electrodes to effect tissue modulation on the target region. The current between the first and second electrodes may be monitored for changes in the impedance of the target region.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

While the devices and methods described herein are discussed relative to renal nerve modulation, it is contemplated that the devices and methods may be used in other applications where nerve modulation and/or ablation are desired. For example, the devices and methods described herein may also be used for prostate ablation, tumor ablation, and/or other therapies requiring heating or ablation of target tissue. In some instances, it may be desirable to ablate perivascular renal nerves with deep target tissue heating. As energy passes from a modulation element to the desired treatment region the energy may heat both the tissue and the intervening fluid (e.g. blood) as it passes. As more energy is used, higher temperatures in the desired treatment region may be achieved thus resulting in a deeper lesion. Monitoring tissue properties may, for example, verify effective ablation, improve safety, and optimize treatment time.

In some instances, ablation is performed with the modulation element in direct contact with the vessel or chamber wall. The modulation element may contain a thermistor or thermocouple which facilitates monitoring of the ablation progress by providing a real-time temperature signal. However, in some instances, it may be advantageous to move the modulation element away from the vessel wall in an off-the-wall configuration, such as when circumferential ablation is desired. During circumferential ablation, the modulation element may be positioned at the center of the lumen. However, when the modulation element does not contact the vessel wall it may be difficult to detect tissue changes during and/or after the ablation process. When provided in an off-the-wall configuration, the modulation element, and thus any temperature sensing means provided on or adjacent to the ablation electrode, may be cooled by the blood flow surrounding the modulation element. As such, thermal feedback may not be useful to provide monitoring as the ablation is performed, resulting in a "blind" ablation scenario. Although the ability to monitor the tissue properties during circumferential ablation may be reduced or require additional sensing elements, off-the-wall ablation may allow for free flow of blood across the vessel surface minimizing heat damage to the vessel wall due to the ablation process.

In some instances, impedance monitoring may be used to detect changes in target tissues as ablation progresses. Sensing electrodes may be provided in addition to the modulation element. In some instances, the impedance may not be directly measured, but may be a function of the current distribution between the sensing electrodes. In general, the resistance of the surrounding tissue may decrease as the temperature of the tissue increases until a point where the tissue begins to denature or irreversibly change, for example, at approximately 50-60° C. Once the tissue has begun to denature the resistance of the tissue may increase.

As the target tissue is ablated, the change in impedance may be analyzed to determine how much tissue has been ablated. The power level and duration of the ablation may be adjusted accordingly based on the impedance of the tissue.

Figure 1:
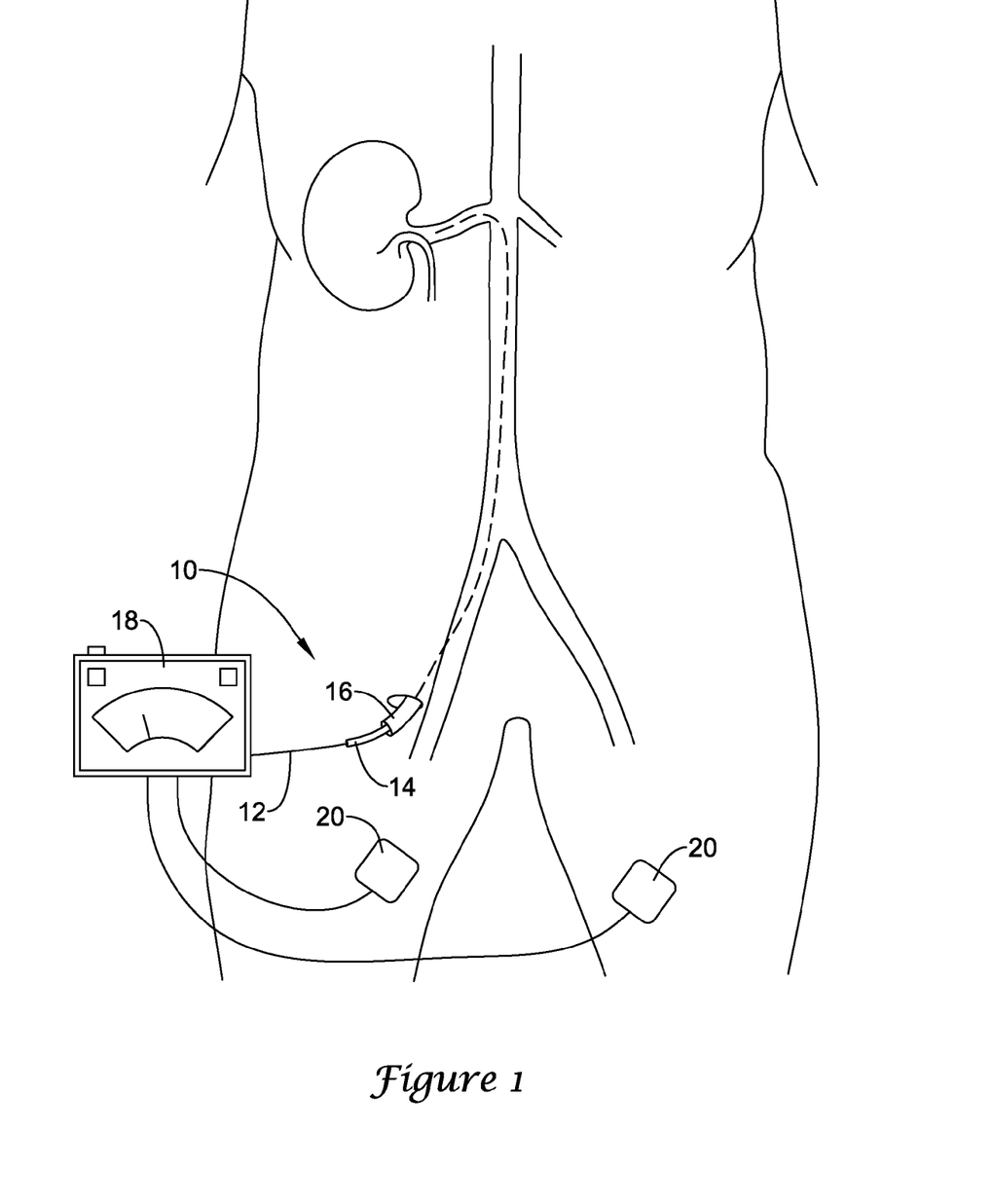
FIG. 1 is a schematic view illustrating a renal nerve modulation system in situ.

FIG. 1 is a schematic view of an illustrative renal nerve modulation system 10 in situ. System 10 may include an element 12 for providing power to a nerve modulation element disposed about and/or within a central elongate shaft 14 and, optionally, within a sheath or guide catheter 16. A proximal end of element 12 may be connected to a control and power element 18, which supplies the necessary electrical energy to activate the one or more modulation elements at or near a distal end of the element 12. In some instances, return electrode patches 20 may be supplied on the legs or at another conventional location on the patient's body to complete the circuit. The control and power element 18 may include monitoring elements to monitor parameters such as power, temperature, voltage, pulse size, and/or shape and other suitable parameters as well as suitable controls for performing the desired procedure. In some instances, the power element 18 may control a radio frequency (RF) ablation electrode and/or one or more sensing electrodes. It is contemplated that more than one power element 18 may be provided. In some instances, the ablation electrode and the sensing electrode may be connected to separate power elements 18. The ablation electrode may be configured to operate at a frequency of approximately 460 kHz. It is contemplated that any desired frequency in the RF range may be used, for example, from 100-500 kHz. However, it is contemplated that different types of energy outside the RF spectrum may be used as desired, for example, but not limited to ultrasound, microwave, and laser to perform the ablation. While the term ablation electrode is used herein, it is contemplated that the modulation element and modulation frequency may be selected according to the energy used to perform the ablation. For example, when ultrasound energy is used, an ultrasonic transducer may be selected as the modulation element and modulation frequencies may be in the MHz range. The sensing electrodes may be configured to operate over frequency ranges which are different from the frequency range at which the ablation is being performed. It is contemplated that the sensing electrodes may be operated over a range of frequencies for improved impedance measuring.

Figure 2:
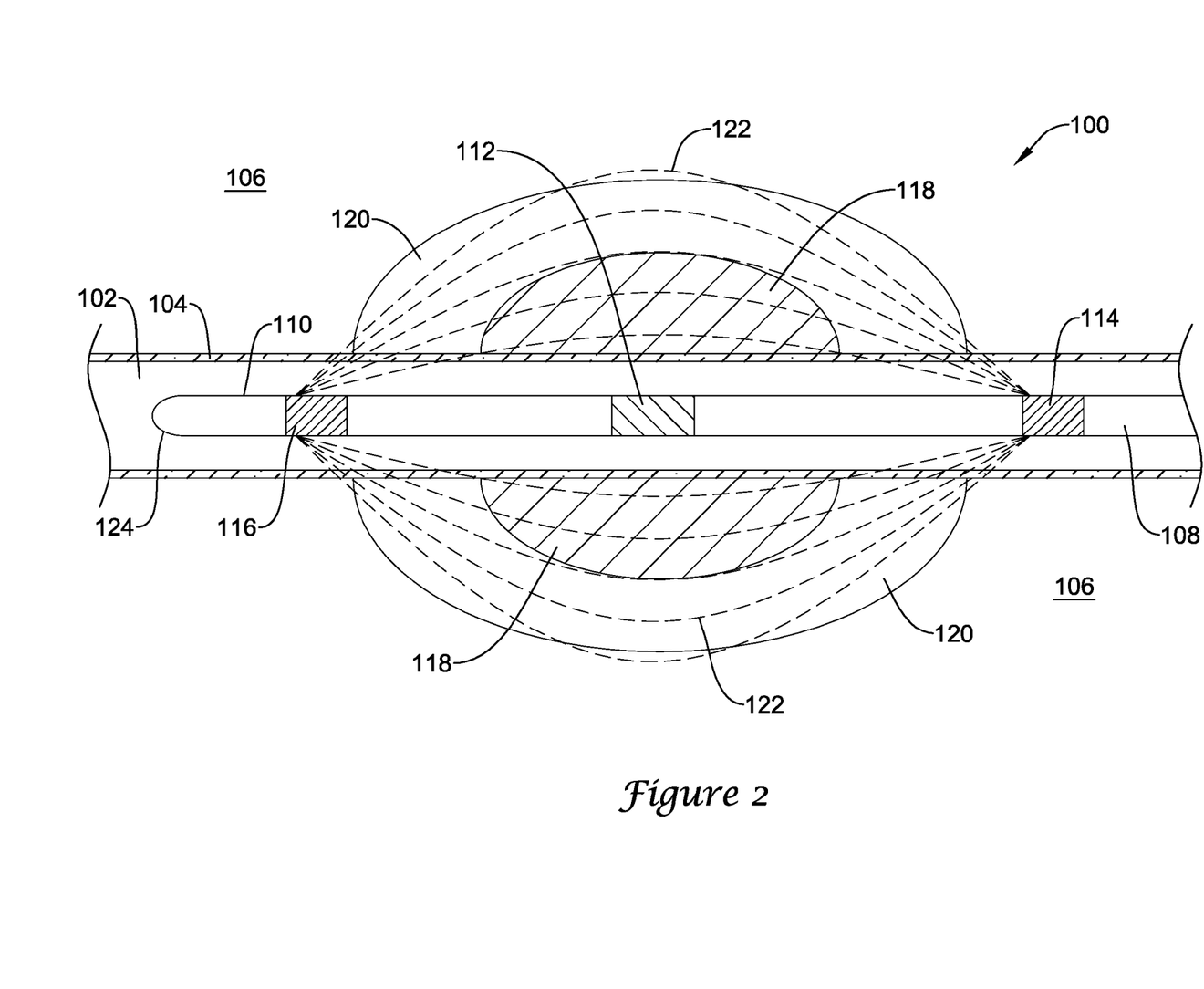
FIG. 2 illustrates a distal end of an illustrative renal nerve modulation system.

FIG. 2 is an illustrative embodiment of a distal end of a renal nerve modulation system 100 disposed within a body lumen 102 having a vessel wall 104. The vessel wall 104 may be surrounded by additional body tissue 106. A portion of the tissue 106 may be the desired treatment region 118, 120, as will be discussed in more detail below. The system 100 may include an elongate shaft 108 having a distal end region 110. The elongate shaft 108 may extend proximally from the distal end region 110 to a proximal end configured to remain outside of a patient's body. The proximal end of the elongate shaft 108 may include a hub attached thereto for connecting other treatment devices or providing a port for facilitating other treatments. It is contemplated that the stiffness of the elongate shaft 108 may be modified to form a modulation system 100 for use in various vessel diameters and various locations within the vascular tree. The elongate shaft 108 may further include one or more lumens extending therethrough. For example, the elongate shaft 108 may include a guidewire lumen and/or one or more auxiliary lumens. The lumens may be configured in any way known in the art. For example, the guidewire lumen may extend the entire length of the elongate shaft 108 such as in an over-the-wire catheter or may extend only along a distal portion of the elongate shaft 108 such as in a single operator exchange (SOE) catheter. These examples are not intended to be limiting, but rather examples of some possible configurations. While not explicitly shown, the modulation system 100 may further include temperature sensors/wire, an infusion lumen, radiopaque marker bands, fixed guidewire tip, a guidewire lumen, external sheath and/or other components to facilitate the use and advancement of the system 100 within the vasculature.

The system 100 may further include one or more ablation electrodes 112 disposed on the outer surface of the elongate shaft 108 adjacent the distal end region 110. However, the ablation electrode 112 may be placed at any longitudinal location along the elongate shaft desired. While the system 100 is illustrated as including one ablation electrode 112, it is contemplated that the modulation system 100 may include any number of ablation electrodes 112 desired, such as, but not limited to, two, three, four, or more. If multiple ablation electrodes 112 are provided, the ablation electrodes 112 may be longitudinally, radially and/or circumferentially spaced as desired. In some instances, the ablation electrode 112 may be a circumferential electrode extending around the outer perimeter of the elongate shaft 108. A circumferential electrode 112 may allow for circumferential ablation while reducing and/or eliminating the need for circumferential repositioning of the electrode 112 and/or elongate shaft 108. In some embodiments, the ablation electrode 112 may not extend all the way around the perimeter of the elongate shaft 108. It is contemplated that multiple ablation electrodes 112 may be circumferentially positioned around the perimeter of the elongate shaft 108 to reduce and/or eliminate the need to circumferentially reposition the elongate shaft 108 to perform 360° ablation.

In some embodiments, the ablation electrode 112 may be formed of a separate structure and attached to the elongate shaft 108. For example, the ablation electrode 112 may be machined or stamped from a monolithic piece of material and subsequently bonded or otherwise attached to the elongate shaft 108. In other embodiments, the ablation electrode 112 may be formed directly on the surface of the elongate shaft 108. For example, the ablation electrode 112 may be plated, printed, or otherwise deposited on the surface. In some instances, the ablation electrode 112 may sufficiently radiopaque so that it also functions as a radiopaque marker. The ablation electrode 112 may be formed from any suitable material such as, but not limited to, platinum, gold, stainless steel, cobalt alloys, or other non-oxidizing materials. In some instances, titanium, tantalum, or tungsten may be used. It is contemplated that the ablation electrode 112 may take any shape desired, such as, but not limited to, square, rectangular, circular, elliptical, etc. In some embodiments, the ablation electrode 112 may have rounded edges in order to reduce the affects of sharp edges on current density. The size of the ablation electrode 112 may be chosen to optimize the current density without increasing the profile of the modulation system 100. For example, an ablation electrode 112 that is too small may generate high local current densities resulting in greater heat transfer to the blood and surrounding tissues. An ablation electrode 112 that is too large may require a larger elongate shaft 108 to carry it. In some instances, the ablation electrode 112 may have an aspect ratio of 2:1 (length to width) or greater. Such an elongated structure may provide the ablation electrode 112 with more surface area without increasing the profile of the modulation system 100.

During the ablation procedure, the ablation electrode 112 may be positioned away from the vessel wall 104 in an off-the-wall configuration. While not explicitly shown, modulation system 100 may further include structure to maintain the ablation electrode 112 in the off-the-wall configuration. For example, in some instances, the elongate shaft may further include a positioning basket configured to expand and engage the vessel wall 104 to center the electrode 112. In other embodiments, elongate shaft 108 may further include a partially occlusive balloon which may be used to position the ablation electrode 112 and/or to increase the blood velocity near the ablation electrode 112 to provide better vessel wall 104 cooling. It is further contemplated that the ablation electrode 112 and/or sensing electrodes 114, 116 may be positioned on a positioning basket and/or balloon.

The modulation system 100 may further include a proximal sensing electrode 114 and a distal sensing electrode 116. The proximal sensing electrode 114 may be located proximal of the ablation electrode 112 and the distal sensing electrode 116 may be located distal of the ablation electrode 112. In some embodiments, the distal sensing electrode 116 may be located proximal of the distal end 124 of the elongate shaft 108. In other embodiments, the distal sensing electrode 116 may be adjacent to the distal end 124 of the elongate shaft 108. While the system is illustrated as including two sensing electrodes 114, 116, it is contemplated that fewer than or more than two sensing electrodes 114, 116 may be provided to improve or provide additional impedance information. In some embodiments, the sensing electrodes may be high-impedance sensing electrodes. This may minimize the field distortion during the measurement. However, in some instances, low-impedance sensing electrodes may be used.

The sensing electrodes 114, 116 may be used to monitor the impedance of the tissue separating them. Impedance sensing current 122 may pass between the proximal 114 and distal 116 sensing electrodes. For clarity, not all of the potential current paths 122 have been illustrated or numbered. For example, it is contemplated that some current may pass through the bloodstream between the sensing electrodes 114, 116. As ablation of the target region 118, 120 progresses, the impedance properties of the surrounding tissue 118, 120 may change thus changing the impedance calculated between the proximal sensing electrode 114 and the distal sensing electrode 116. The sensing electrodes 114, 116 may be symmetrically placed about the ablation electrode 112 such that they can easily track the change which occurs to the tissue impedance in the ablation zone 118, 120 located between them. This may provide improved signal-to-noise ratio for better real-time monitoring of the ablation progress. However, the sensing electrodes 114, 116 may be arranged in any orientation desired and need not be symmetrical about the ablation electrode 112. While the sensing electrodes 114, 116 are illustrated in a non-contact ablation system 100 it is contemplated that the sensing electrodes 114, 116 may be used in systems where the ablation electrode 112 contacts the vessel wall 104.

In some embodiments, the sensing electrodes 114, 116 may be formed of a separate structure and attached to the elongate shaft 108. For example, the sensing electrodes 114, 116 may be machined or stamped from a monolithic piece of material and subsequently bonded or otherwise attached to the elongate shaft 108. In other embodiments, sensing electrodes 114, 116 may be formed directly on the surface of the elongate shaft 108. For example, the sensing electrodes 114, 116 may be plated, printed, or otherwise deposited on the surface. In some instances, the sensing electrodes 114, 116 may also function as radiopaque marker bands. The sensing electrodes 114, 116 may be formed from any suitable material such as, but not limited to, platinum, gold, stainless steel, cobalt alloys, or other non-oxidizing materials. In some instances, titanium, tantalum, or tungsten may be used. It is contemplated that the sensing electrodes 114, 116 may take any shape desired, such as, but not limited to, square, rectangular, circular, oblong, etc. The size of the sensing electrodes 114, 116 may be chosen to optimize the current density without increasing the profile of the modulation system 100.

While not explicitly shown, the sensing electrodes 114, 116 may be connected to the control unit (such as control unit 18 in FIG. 1) by electrical conductors. In some embodiments the sensing electrodes 114, 116 may be on a separate electrical circuit from the ablation electrode 112 and from each other. The sensing electrodes 114, 116 may be operated at a different frequency than the ablation electrode 112. For example, the frequency, duty cycle, and shape of the excitation waveform of the sensing electrodes 114, 116 can be adapted to yield an optimized signal-to-noise ratio for each of the tissue parameters monitored. In some instances, the sensing electrodes 114, 116 may be operated simultaneously with the ablation electrode 112 to provide real-time feedback of the ablation progress. In other embodiments, the sensing electrodes 114, 116 may be operated in an alternating fashion (e.g. an ablation/sensing duty cycle) with the ablation electrode 112 such that the sensing electrodes 114, 116 and the ablation electrode 112 are not simultaneously active.

While not explicitly shown, the ablation electrode 112 may be connected to a control unit (such as control unit 18 in FIG. 1) by electrical conductors. Once the modulation system 100 has been advanced to the treatment region, energy may be supplied to the ablation electrode 112. The amount of energy delivered to the ablation electrode 112 may be determined by the desired treatment as well as the feedback obtained from the sensing electrodes 114, 116. As discussed above, once the target tissue 118, 120 has begun to denature the resistance of the tissue may increase. The target region 118 nearest the ablation electrode 112 may receive more energy than the target region 120 positioned further away from the ablation electrode 112 and thus may begin to denature more quickly. As the target tissue 118, 120 is ablated, the change in impedance in the tissue 118, 120 may be analyzed to determine how much tissue has been ablated and/or the degree of denaturing. The power level and duration of the ablation may be adjusted accordingly based on the impedance of the tissue. For example, more energy may result in a larger, deeper lesion.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide sheath such as the sheath 16 shown in FIG. 1. Once the ablation electrode 112 of the modulation system 100 has been placed adjacent to the desired treatment area, positioning mechanisms may be deployed, if so provided. While not explicitly shown, the ablation electrode 112 and the sensing electrodes 114, 116 may be connected to a single control unit or to separate control units (such as control unit 18 in FIG. 1) by electrical conductors. Once the modulation system 100 has been advanced to the treatment region, energy may be supplied to the ablation electrode 112 and the sensing electrodes 114, 116. As discussed above, the energy may be supplied to both the ablation electrode 112 and sensing electrodes 114, 116 simultaneously or in an alternating fashion at desired. The amount of energy delivered to the ablation electrode 112 may be determined by the desired treatment as well as the feedback provided by the sensing electrodes 114, 116.

It is contemplated if an ablation electrode 112 is provided that does not extend around the entire circumference of the elongate shaft 108, the elongate shaft 108 may need to be circumferentially repositioned and energy may once again be delivered to the ablation electrode 112 and the sensing electrodes 114, 116 to adequately ablate the target tissue. The number of times the elongate shaft 108 is rotated at a given longitudinal location may be determined by the number and size of the ablation electrode(s) 112 on the elongate shaft 108. Once a particular location has been ablated, it may be desirable to perform further ablation procedures at different longitudinal locations. Once the elongate shaft 108 has been longitudinally repositioned, energy may once again be delivered to the ablation electrode 112, and the sensing electrodes 114, 116. If necessary, the elongate shaft 108 may be circumferentially repositioned at each longitudinal location. This process may be repeated at any number of longitudinal locations desired. It is contemplated that in some embodiments, the system 100 may include ablation electrodes 112 at various positions along the length of the modulation system 100 such that a larger region may be treated without longitudinal displacement of the elongate shaft 108.

While FIG. 2 illustrates the sensing electrodes 114, 116 in an off-the-wall configuration, is contemplated that one or both of the sensing electrodes 114, 116 may be placed in direct contact with the vessel wall 104. As the sensing electrodes 114, 116 may be operated at a frequency and amplitude which does not result in tissue ablation, placing the sensing electrodes 114, 116 against the vessel wall 104 will not cause the vessel damage. In instances where direct contact ablation is acceptable, the ablation electrode 112 may also be placed in contact with the vessel wall 104. It is contemplated that the elongate shaft 108 may further include an infusion lumen configured to perfuse the vessel lumen 102 with saline or other conductive fluid during the ablation procedure. In some instances, the perfused fluid may be provided at room temperature or cooler.

Figure 3:
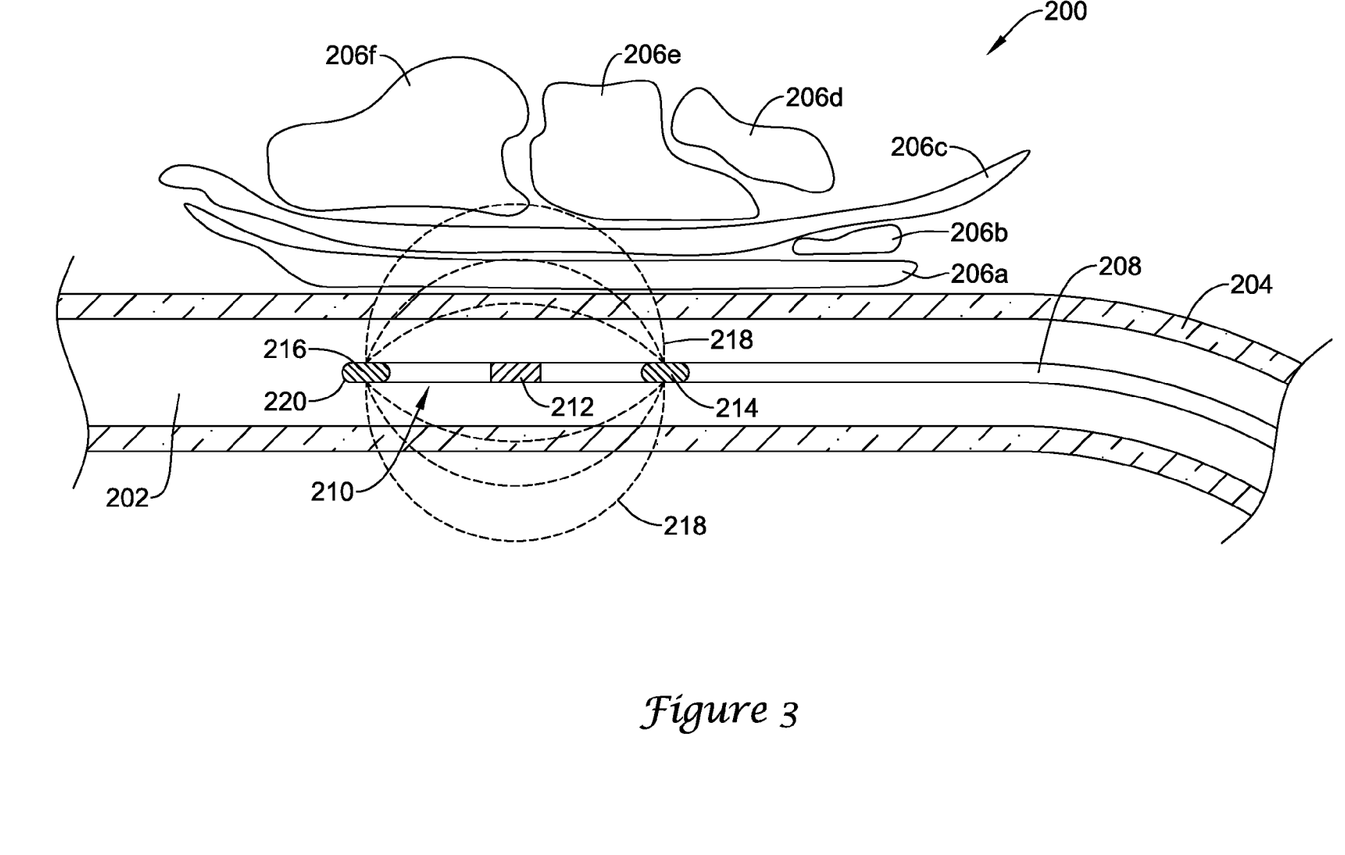
FIG. 3 illustrates a distal end of another illustrative renal nerve modulation system.

FIG. 3 is an illustrative embodiment of a distal end of a renal nerve modulation system 200 that may be similar in form and function to other systems disclosed herein. The modulation system may be disposed within a body lumen 202 having a vessel wall 204. The vessel wall 204 may be surrounded by additional body tissues 206a-f. There may be several different tissue types 206a-f surrounding the vessel wall 204. For example, the tissues 206a-f may comprise adventitia and connective tissues, nerves, fat, fluid, etc. in addition to the muscular vessel wall 204. It is contemplated that some of the body tissues 206a-f may be the same type of tissue or may be all different types of tissue. The body tissues 206a-f shown in FIG. 3 is not intended to fully represent the tissue composition surrounding a vessel wall 204, but rather illustrate that different tissue types and sizes may surround the vessel wall 204. It is to be further understood that while FIG. 3 illustrated the body tissues 206a-f on a single side of the vessel wall, the body tissues 206a-f may surround the perimeter of the vessel wall 204 and is not limited to one side.

Each of the different types of tissue 206a-f may have different electrical properties (e.g. impedance, permittivity, conductivity, etc.) and may also have different changes in those properties due to thermal ablation. Variation in local tissue types 206a-f and impedance may cause unpredictable variation in the ablation effect on the target tissue and in local artery wall heating. It may be desirable to characterize local tissues and monitor tissue changes in order to control the energy delivery for proper target tissue ablation. The nerve modulation system 200 may include two or more sensing electrodes 214, 216 to determine one or more impedance values over a range of frequencies. It is contemplated that tissue impedance may be monitored during RF, ultrasound, laser, microwave, or other ablation. The frequency at which the sensing electrodes 214, 216 are operated may be chosen according to the tissue material present or expected to be present. The impedance may be used to evaluate which type(s) of tissue are adjacent to the ablation region and to monitor changes which occur by thermal ablation of that tissue(s).

The system 200 may include an elongate shaft 208 having a distal end region 210 and a distal end 220. The elongate shaft 208 may extend proximally from the distal end 220 to a proximal end configured to remain outside of a patient's body. The proximal end of the elongate shaft 208 may include a hub attached thereto for connecting other treatment devices or providing a port for facilitating other treatments. It is contemplated that the stiffness of the elongate shaft 208 may be modified to form modulation system 200 for use in various vessel diameters. The elongate shaft 208 may further include one or more lumens extending therethrough. For example, the elongate shaft 208 may include a guide wire lumen and/or one or more auxiliary lumens. The lumens may be configured in any suitable way such as those ways commonly used for medical devices. While not explicitly shown, the modulation system 200 may further include temperature sensors/wire, an infusion lumen, radiopaque marker bands, fixed guidewire tip, external sheath and/or other components to facilitate the use and advancement of the system 200 within the vasculature.

The system 200 may further include one or more ablation electrodes 212 disposed on the outer surface of the elongate shaft 208. While the system 200 is illustrated as including a single ablation electrode 212, it is contemplated that the modulation system 200 may include any number of ablation electrodes 212 desired, such as, but not limited to, two, three, four, or more. If multiple ablation electrodes 212 are provided, the ablation electrodes 212 may be longitudinally and/or radially spaced as desired. The ablation electrode 212 may include similar features and may function in a similar manner to the ablation electrode discussed with respect to FIG. 2.

During the ablation procedure, the ablation electrode 212 may be positioned away from the vessel wall 204 in an off-the-wall configuration. While not explicitly shown, the modulation system 200 may further include structure to maintain the ablation electrode 212 in the off-the-wall configuration. For example, in some instances the elongate shaft may further include a positioning basket configured to expand and engage the vessel wall 204 to center the electrode 212. In other embodiments elongate shaft 208 may further include a partially occlusive balloon which may be used to position the ablation electrode 212 and/or to increase the blood velocity near the ablation electrode 212 to provide better vessel wall cooling. It is further contemplated that the ablation electrode 212 and/or sensing electrodes 214, 216 may be positioned on a positioning basket and/or balloon.

The modulation system 200 may further include a proximal sensing electrode 214 and a distal sensing electrode 216. It is contemplated that the modulation system 200 may include more than two sensing electrodes 214, 216 to further refine the tissue evaluation. The sensing electrodes 214, 216 may include similar features and may function in a similar manner to the sensing electrodes discussed with respect to FIG. 2. In some instances, high impedance sensing electrodes 214, 216 may be used in order to avoid significant distortion of the electric field and to avoid bipolar ablation between the ablation electrode 212 and the sensing electrodes 214, 216. The proximal sensing electrode 214 may be located proximal of the ablation electrode 212 and the distal sensing electrode 216 may be located distal of the ablation electrode 212. In some embodiments, the distal sensing electrode 216 may be located adjacent to the distal end 220 of the elongate shaft 208. In other embodiments, the distal sensing electrode 216 may be proximal of the distal end 220 of the elongate shaft 208.

The sensing electrodes 214, 216 may be used to monitor the impedance of the tissue separating them. While not explicitly shown, the sensing electrodes 214, 216 may be connected through separate insulated conductors to a control unit (such as control unit 18 illustrated in FIG. 1). In some embodiments the sensing electrodes 214, 216 may be on a separate electrical circuit from the ablation electrode 212. The sensing electrodes 214, 216 may be operated at a different frequency than the ablation electrode 212. For example, the frequency, duty cycle, and shape of the excitation waveform of the sensing electrodes 214, 216 can be adapted to yield an optimized signal-to-noise ratio for each of the tissue parameters monitored. When voltage is applied across the sensing electrodes 214, 216, a small current 218 may flow through the tissues 206a-f. For clarity, not all of the potential current paths 218 have been illustrated or numbered. For example, it is contemplated that some current may pass through the bloodstream in lumen 202. The current 218 may be monitored by the control unit and used to determine the local tissue impedance in the vicinity of the sensing electrodes 214, 216. Various frequencies may be used to determine one or more impedance values, or a simpler calculation of resistance at low frequently can be utilized. Tissue impedance may vary at different temperatures and may also be affected by protein changes, perfusion changes, and fluid changes as a result of thermal ablation. The different tissues have different electrical properties and also react differently to thermal ablation. The impedance measurements may be used to determine which tissues are in the local ablation region, and to monitor changes which occur by ablation of those tissues. The use of various frequencies may allow for better discrimination between tissue types and monitoring of ablative changes. Accordingly, ongoing impedance monitoring may be used to evaluate whether the modulation system 200 and positioned appropriately treat target tissue and determine when ablation has been completed. It is contemplated that undesired changes, such as ablative changes to the muscular vessel wall 204, can also be detected.

Tissue impedance may be monitored during simultaneous RF ablation (e.g. energy is applied simultaneously to the ablation electrode 212 and the sensing electrodes 214, 216). In such a case, most of the current may flow between the ablation electrode 212 and a skin contact ground pad (such as ground contact pad 20 in FIG. 1) and through the perivascular target tissues to be ablated, while a small amount of current may flow between the ablation electrode 212 and at least one higher impedance sensing electrode 214, 216. In this instance, it is contemplated that body impedance between the ablation electrode 212 and skin contact ground pad may also be measured. It is further contemplated that tissue impedance may be monitored during ablation/sensing duty cycle which may be used alternate between ablation and impedance measurement. As ablation of the target region progresses, the impedance properties of the surrounding tissues 206a-f may change thus changing the impedance calculated between the proximal sensing electrode 214 and the distal sensing electrode 216, between the ablation electrode 212 and the contact ground pad, and/or between the ablation electrode 212 and one or more sensing electrodes 214, 216.

While not explicitly shown, the ablation electrode 212 may be connected to a control unit (such as control unit 18 in FIG. 1) by electrical conductors. Once the modulation system 200 has been advanced to the treatment region, energy may be supplied to the ablation electrode 212. The amount of energy delivered to the ablation electrode 212 may be determined by the desired treatment as well as the feedback obtained from the sensing electrodes 214, 216. As discussed above, once the target tissue has begun to denature the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 200 may monitor impedance values of the surrounding tissues 206a-f prior to beginning the ablation procedure and adjust the ablation parameters accordingly. It is further contemplated that other electrical properties of the tissues 206a-f such as permittivity and/or conductivity may be used to set the current and/or power for RF or other ablation energy to target tissues.

The modulation system 200 may be advanced through the vasculature in any manner known in the art. For example, system 200 may include a guidewire lumen to allow the system 200 to be advanced over a previously located guidewire. In some embodiments, the modulation system 200 may be advanced, or partially advanced, within a guide sheath such as the sheath 16 shown in FIG. 1. Once the ablation electrode 212 of the modulation system 200 has been placed adjacent to the desired treatment area, positioning mechanisms may be deployed, if so provided. While not explicitly shown, the ablation electrode 212 and the sensing electrodes 214, 216 may be connected to a single control unit or to separate control units (such as control unit 18 in FIG. 1) by electrical conductors. Once the modulation system 200 has been advanced to the treatment region, energy may be supplied to the ablation electrode 212 and the sensing electrodes 214, 216. As discussed above, the energy may be supplied to both the ablation electrode 212 in sensing electrodes 214, 216 simultaneously or in an alternating duty cycle at desired. The amount of energy delivered to the ablation electrode 212 may be determined by the desired treatment as well as the feedback provided by the sensing electrodes 214, 216.

It is contemplated if an ablation electrode 212 is provided that does not extend around the entire circumference of the elongate shaft 208, the elongate shaft 208 may need to be circumferentially repositioned and energy may once again be delivered to the ablation electrode 212 and the sensing electrodes 214, 216 to adequately ablate the target tissue ablation. The number of times the elongate shaft 208 is rotated at a given longitudinal location may be determined by the number and size of the ablation electrode(s) 212 on the elongate shaft 208. Once a particular location has been ablated, it may be desirable to perform further ablation at different longitudinal locations. Once the elongate shaft 208 has been longitudinally repositioned, energy may once again be delivered to the ablation electrode 212, and the sensing electrodes 214, 216. If necessary, the elongate shaft 208 may be circumferentially repositioned at each longitudinal location. This process may be repeated at any number of longitudinal locations desired. It is contemplated that in some embodiments, the system 200 may include ablation electrodes 212 at various positions along the length of the modulation system 200 such that a larger region may be treated without longitudinal displacement of the elongate shaft 208.

While FIG. 3 illustrates the sensing electrodes 214, 216 in an off-the-wall configuration, it is contemplated that one or both of the sensing electrodes 214, 216 may be placed in direct contact with the vessel wall 204. As the sensing electrodes 214, 216 may be operated at a frequency and amplitude which does not result in tissue ablation, placing the sensing electrodes 214, 216 against the vessel wall 204 will not cause the vessel damage. In instances where direct contact ablation is acceptable, the ablation electrode 212 may also be placed in contact with the vessel wall 204. It is contemplated that the elongate shaft 208 may further include an infusion lumen configured to perfuse the vessel lumen 202 with saline or other conductive fluid during the ablation procedure. In some instances, the perfused fluid may be provided at room temperature or cooler.

Figure 4:
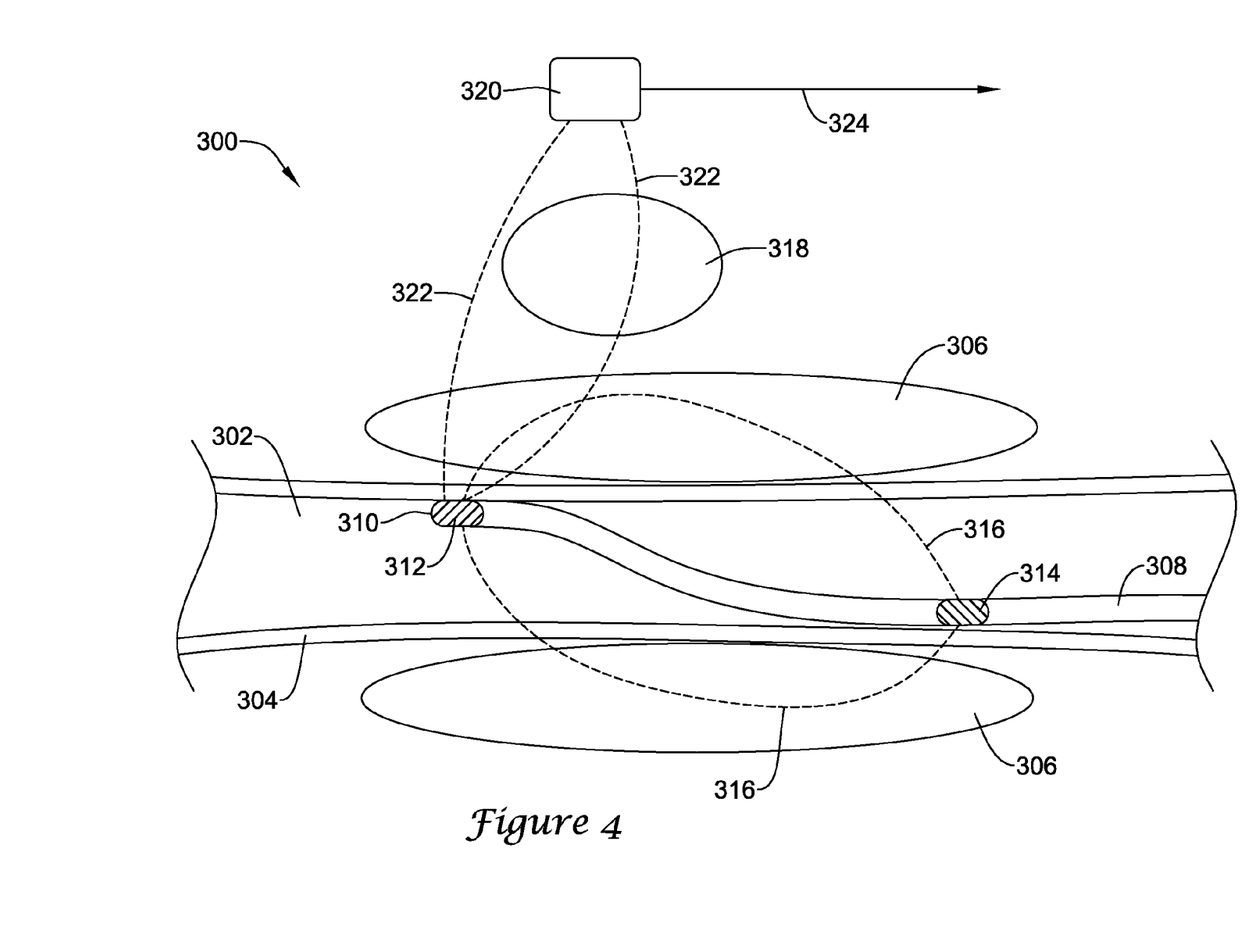
FIG. 4 illustrates a distal end of another illustrative renal nerve modulation system.

FIG. 4 is an illustrative embodiment of a distal end of a renal nerve modulation system 300 that may be similar in form and function to other systems disclosed herein. The modulation system 300 may be disposed within a body lumen 302 having a vessel wall 304. The vessel wall 304 may be surrounded by local target tissue 306. It may be desirable to determine local tissue impedance and monitor tissue changes in order to control the energy delivery for proper target tissue ablation. The nerve modulation system 300 may include a high-impedance sensing electrode 314 to determine local impedance. It is contemplated that tissue impedance may be monitored during RF, ultrasound, laser, microwave, or other ablation methods.

The system 300 may include an elongate shaft 308 having a distal end 310. The elongate shaft 308 may extend proximally from the distal end 310 to a proximal end configured to remain outside of a patient's body. The proximal end of the elongate shaft 308 may include a hub attached thereto for connecting other treatment devices or providing a port for facilitating other treatments. It is contemplated that the stiffness of the elongate shaft 308 may be modified to form modulation system 300 for use in various vessel diameters. The elongate shaft 308 may further include one or more lumens extending therethrough. For example, the elongate shaft 308 may include a guide wire lumen and/or one or more auxiliary lumens. The lumens may be configured in any suitable way such as those ways commonly used for medical devices. While not explicitly shown, the modulation system 300 may further include temperature sensors/wires, an infusion lumen, radiopaque marker bands, fixed guidewire tip, external sheath and/or other components to facilitate the use and advancement of the system 300 within the vasculature.

The system 300 may further include one or more ablation electrodes 312 disposed on the outer surface of the elongate shaft 308. While the system 300 is illustrated as including one ablation electrode 312, it is contemplated that the modulation system 300 may include any number of ablation electrodes 312 desired, such as, but not limited to, two, three, four, or more. If multiple ablation electrodes 312 are provided, the ablation electrodes 312 may be longitudinally and/or radially and/or circumferentially spaced as desired. The ablation electrode 312 may include similar features and may function in a similar manner to the ablation electrode discussed with respect to FIG. 2. In some embodiments, the ablation electrode 312 may be positioned adjacent to the distal end 310 of the elongate shaft 308. In other embodiments, the ablation electrode 312 may be positioned proximal of the distal end 310.

The modulation system 300 may further include a sensing electrode 314. It is contemplated that the modulation system 300 may include more than one sensing electrode 314 to further refine the tissue evaluation. The sensing electrode 314 may include similar features and may function in a similar manner to the sensing electrode discussed with respect FIG. 2. In some instances, a high impedance sensing electrode 314 may be used in order to avoid significant distortion of the electric field and to avoid bipolar ablation between the ablation electrode 312 and the sensing electrode 314. In some embodiments, the sensing electrode 314 may be located proximal of the ablation electrode 312. In other embodiments, the sensing electrode 314 may be located distal of the ablation electrode 312.

The ablation electrode 312 and the sensing electrode 314 may be used to monitor the impedance of the local tissue 306. While not explicitly shown, the ablation electrode 312 and the sensing electrode 314 may be connected through separate insulated conductors to a control unit (such as control unit 18 in FIG. 1). A skin-contact ground pad 320 may also be connected through an electrical conductor 324 to the control unit. As voltage is applied to the ablation electrode 312, current 322 may pass through the local tissue 306 and additional body tissue 318 to the ground pad 320. During ablation, the sensing electrode 314 may be used as a reference electrode and measure the local voltage at a known location in the local tissue 306, which may be monitored by the control unit. The local voltage may be used to determine the local tissue impedance between the ablation electrode 312 and the sensing electrode 314. Various frequencies may be used to determine one or more impedance values, or a simpler calculation of resistance at low frequency can be utilized.

Tissue impedance may be monitored during simultaneous RF ablation (e.g. energy is applied simultaneously to the ablation electrode 312 and the sensing electrodes 314). In such a case, most of the current 322 may flow between the ablation electrode 312 and the skin-contact ground pad 320 and through the perivascular target tissues to be ablated, while a small amount of current 316 may flow between the ablation electrode 312 and the high impedance sensing electrode 314. In this instance, the body impedance resulting from body tissue 318 outside of the target tissue region 306 between the ablation electrode 312 and skin contact ground pad 320 may also be measured. Tissue distribution and make-up may vary from patient to patient. For example, in some instances, a large portion of the power applied to the system 300 (e.g. approximately 80% in some cases) may be distributed locally, or within approximately two to three radii of in the ablation electrode 312, while the remaining portion (e.g. approximately 20%) is distributed throughout the remainder of the body (e.g across the skin, subcutaneous fat, and/or other tissue not in the local target tissue 306). As the body composition may vary from person to person, the power distribution may also vary. The modulation system 300 may be configured to normalize the voltage supplied to the ablation electrode 312 to account for variations in impedance of the patient's body. It is contemplated that the local voltage (e.g. the difference between the voltage at the ablation electrode 312 and the voltage at the sensing electrode 314) may be used to determine the local power density (e.g. the power density adjacent to the ablation electrode 312). For example, the local power density may be determined by the Equation 1:

$$P_{loc} = I\Delta V \tag{1}$$

where $P_{loc}$ is the local power density, I is the current, and $\Delta V$ is the difference between the voltage at the ablation electrode 312 and the voltage at the sensing electrode 314. The local power density may then be used to adjust the power delivery of the system 300 to achieve the desired tissue modulation.

It is further contemplated that tissue impedance may be monitored during an ablation/sensing duty cycle which may be used alternate between ablation and impedance measurements. As ablation of the target region progresses, the impedance properties of the local tissue 306 may change thus changing the impedance calculated between the ablation electrode 312 and the contact ground pad 320 and/or between the ablation electrode 312 and the sensing electrode 314. It is contemplated that poor ground pad 320 contact may also be detected during the ablation process.

While not explicitly shown, the ablation electrode 312 may be connected to a control unit (such as control unit 18 in FIG. 1) by electrical conductors. Once the modulation system 300 has been advanced to the treatment region, energy may be supplied to the ablation electrode 312. The amount of energy delivered to the ablation electrode 312 may be determined by the desired treatment as well as the feedback obtained from the sensing electrodes 314. Once the target tissue has begun to rise in temperature, and/or denature, the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 300 may monitor impedance values of the surrounding tissue 306 prior to beginning the ablation procedure and adjust the ablation parameters accordingly. It is further contemplated that other electrical properties of the local tissue 306 such as permittivity and/or conductivity may be used to set the current and/or power for RF or other sources of ablation energy to target tissues.

The modulation system 300 may be advanced through the vasculature in any manner known in the art. For example, system 300 may include a guidewire lumen to allow the system 300 to be advanced over a previously located guidewire. In some embodiments, the modulation system 300 may be advanced, or partially advanced, within a guide sheath such as the sheath 16 shown in FIG. 1. Once the ablation electrode 312 of the modulation system 300 has been placed adjacent to the desired treatment area, positioning mechanisms may be deployed, if so provided. For example, in some embodiments, the elongate shaft 308 may include push and/or pull wires to deflect a distal end region of the elongate shaft 308. For example, a push and/or pull wire may be attached adjacent to the distal end 310 of the elongate shaft 308 and then extend along an outer surface of the elongate shaft 308 or along an interior passageway formed in the shaft 308 to a position where it is accessible to a user. In other embodiments, the elongate shaft 308 may incorporate a planar deflection mechanism, such as a rib and spine mechanism. However, it is contemplated that the elongate shaft 308 may be deflected in any desired manner. The ablation electrode 312 and the sensing electrode 314 may be positioned adjacent to the deflectable region of the elongate shaft 308. Deflection of the elongate shaft 308 may position the ablation electrode 312 adjacent a first target region and the sensing electrode 314 adjacent a second target region.

As discussed above, the ablation electrode 312 and the sensing electrode 314 may be connected to a control unit (such as control unit 18 in FIG. 1) by insulated electrical conductors. Once the modulation system 300 has been advanced to the treatment region, energy may be supplied to the ablation electrode 312. As discussed above, the energy may be supplied to both the ablation electrode 312 and/or the sensing electrode 314 simultaneously or in an alternating duty cycle as desired. The amount of energy delivered to the ablation electrode 312 may be determined by the desired treatment as well as the feedback provided by the sensing electrode 314.

It is contemplated if an ablation electrode 312 is provided that does not extend around the entire circumference of the elongate shaft 308, the elongate shaft 308 may need to be circumferentially repositioned and energy may once again be delivered to the ablation electrode 312 to adequately ablate the target tissue. The number of times the elongate shaft 308 is rotated at a given longitudinal location may be determined by the number and size of the ablation electrode (s) 312 on the elongate shaft 308. Once a particular location has been ablated, it may be desirable to perform further ablation at different longitudinal locations. Once the elongate shaft 308 has been longitudinally repositioned, energy may once again be delivered to the ablation electrode 312. If necessary, the elongate shaft 308 may be circumferentially repositioned at each longitudinal location. This process may be repeated at any number of longitudinal locations desired. It is contemplated that in some embodiments, the system 300 may include ablation electrodes 312 at various positions along the length of the modulation system 300 such that a larger region may be treated without longitudinal displacement of the elongate shaft 308.

While FIG. 4 illustrates the ablation electrode 312 and the sensing electrode 314 in direct contact with the vessel wall, it is contemplated that the ablation electrode 312 and/or the sensing electrode 314 may be positioned away from the vessel wall 304 in an off-the-wall configuration. While not explicitly shown, the modulation system 300 may further include structure to maintain the ablation electrode 312 in the off-the-wall configuration. For example, in some instances the elongate shaft may further include a positioning basket configured to expand and engage the vessel wall 304 to center the electrode 312. In other embodiments elongate shaft 308 may further include a partially occlusive balloon which may be used to position the ablation electrode 312 and/or to increase the blood velocity near the ablation electrode 312 to provide better vessel wall cooling. It is contemplated that the elongate shaft 308 may further include an infusion lumen configured to perfuse the vessel lumen 302 with saline or other conductive fluid during the ablation procedure. In some instances, the perfused fluid may be provided at room temperature or cooler.

Figure 5:
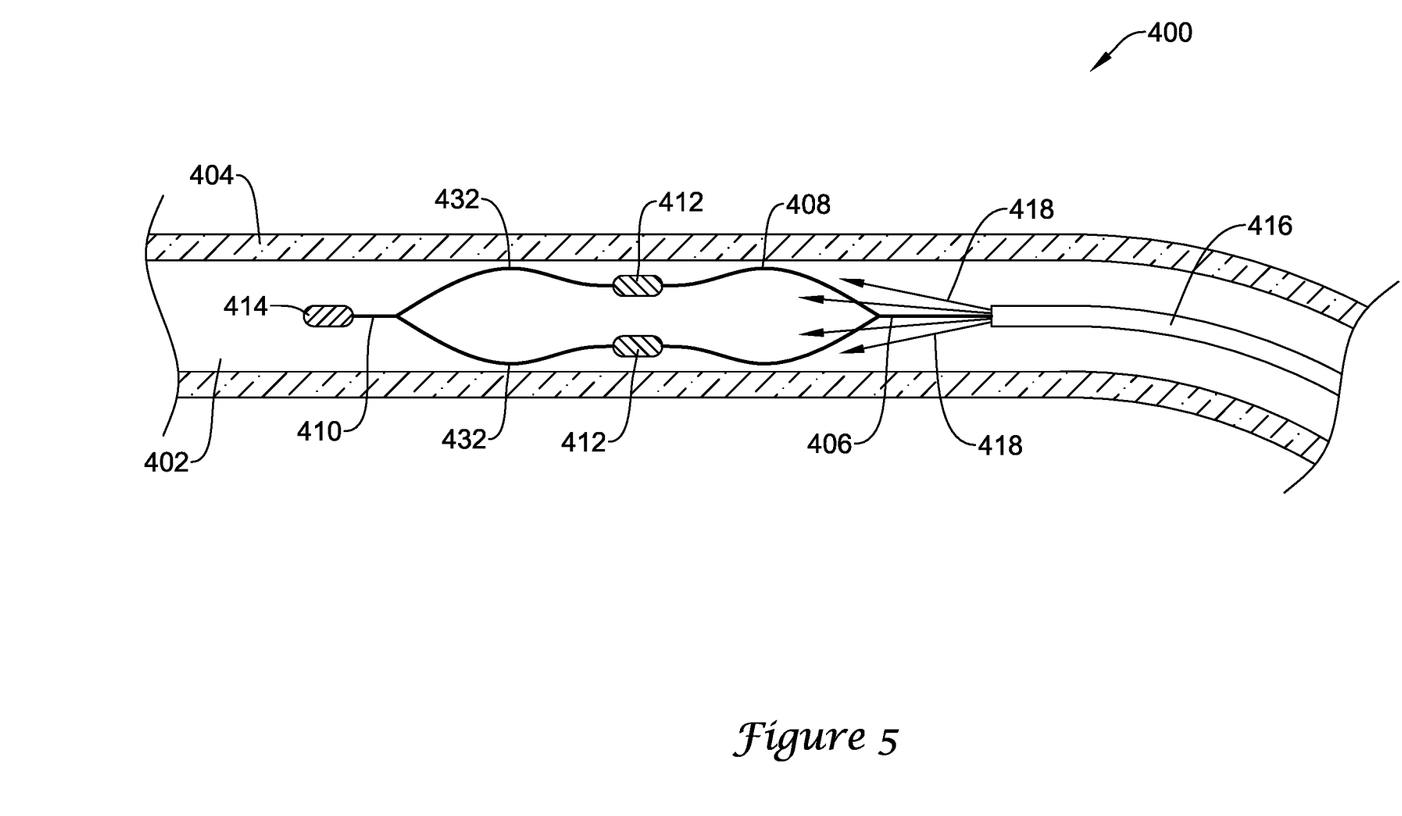
FIG. 5 illustrates a distal end of another illustrative renal nerve modulation system.

FIG. 5 is another illustrative embodiment of a distal end of a renal nerve modulation system 400 that may be similar in form and function to other systems disclosed herein. The modulation system 400 may be disposed within a body lumen 402 having a vessel wall 404. The vessel wall 404 may be surrounded by local target tissue. It may be desirable to determine local tissue impedance and monitor tissue changes in order to control energy delivery for proper target tissue ablation. The nerve modulation system 400 may include a high-impedance or low-impedance sensing electrode 414 to determine local impedance in the target tissue and surrounding blood. It is contemplated that tissue impedance may be monitored during RF, ultrasound, laser, microwave, or other ablation methods.

The system 400 may include an elongate member 406 having an expandable framework 408 disposed adjacent the distal end region 410. In some instances, the modulation system 400 may include an expandable balloon in place of the expandable framework 408. It is further contemplated that the modulation system 400 may not include an expandable portion. The elongate member 406 may extend proximally from the distal end region 410 to a proximal end configured to remain outside of a patient's body. The proximal end of the elongate member 406 may include a hub attached thereto for connecting other treatment devices or providing a port for facilitating other treatments. It is contemplated that the stiffness of the elongate member 406 may be modified to form modulation system 400 for use in various vessel diameters. In some instances, the elongate member 406 may be a wire having a generally solid cross-section. In other embodiments, the elongate member 406 may include one or more lumens extending therethrough. For example, the elongate member 406 may include a guide wire lumen and/or one or more auxiliary lumens. The lumens may be configured in any suitable way such as those ways commonly used for medical devices. While not explicitly shown, the modulation system 400 may further include temperature sensors/wires, an infusion lumen, radiopaque marker bands, fixed guidewire tip, external sheath and/or other components to facilitate the use and advancement of the system 400 within the vasculature.

The system 400 may further include one or more ablation electrodes 412 disposed on the expandable framework 408. The ablation electrodes 412 may be positioned on separate struts 432 of the expandable framework 408 such that the when the framework 408 is expanded the ablation electrodes 412 are positioned adjacent to opposite sides of the vessel wall 404. While the system 400 is illustrated as including two ablation electrodes 412, it is contemplated that the modulation system 400 may include any number of ablation electrodes 412 desired, such as, but not limited to, one, three, four, or more. If multiple ablation electrodes 412 are provided, the ablation electrodes 412 may be longitudinally and/or radially and/or circumferentially spaced as desired. In some instances, the ablation electrodes 412 may be positioned to be adjacent to opposite sides of the vessel 404. The ablation electrodes 412 may include similar features and may function in a similar manner to the ablation electrode discussed with respect to FIG. 2. In some embodiments, the ablation electrodes 412 may be positioned proximal of the distal end region 410 of the elongate member 406. In other embodiments, the ablation electrodes 412 may be positioned adjacent to the distal end region 410. It is further contemplated that the ablation electrodes 412 may function as both ablation and sensing electrodes.

The modulation system 400 may further include a sensing electrode 414. It is contemplated that the modulation system 400 may include more than one sensing electrode 414 to further refine the tissue evaluation. The sensing electrode 414 may include similar features and may function in a similar manner to the sensing electrode discussed with respect FIG. 2. In some instances, a high impedance sensing electrode 414 may be used in order to avoid significant distortion of the electric field and to avoid bipolar ablation between the ablation electrode 412 and the sensing electrode 414. In other instances, a low-impedance sensing electrode 414 may be used. In some embodiments, the sensing electrode 414 may be located distal of the ablation electrodes 412 and adjacent to the distal end region 410. In other embodiments, the sensing electrode 414 may be located proximal of the ablation electrodes 412.

The ablation electrodes 412 and the sensing electrode 414 may be used to monitor the impedance of the local tissue. While not explicitly shown, the ablation electrode 412 and the sensing electrode 414 may be connected through separate insulated conductors to a control unit (such as control unit 18 in FIG. 1). In some instances, the ablation electrodes 412 may be used as sensing electrodes to determine local tissue impedance. The ablation electrodes 412 may be spaced a distance from the sensing electrode 414 such that voltage applied to the electrodes 412, 414 may cause current to flow between the electrodes 412, 414 through the blood and nearby tissues. Measurement of the current may allow the resistance or complex impedance of the blood and tissue to be calculated. Various frequencies may be used to determine one or more impedance values, or a simpler calculation of resistance at low frequency can be utilized.

Figure 6:
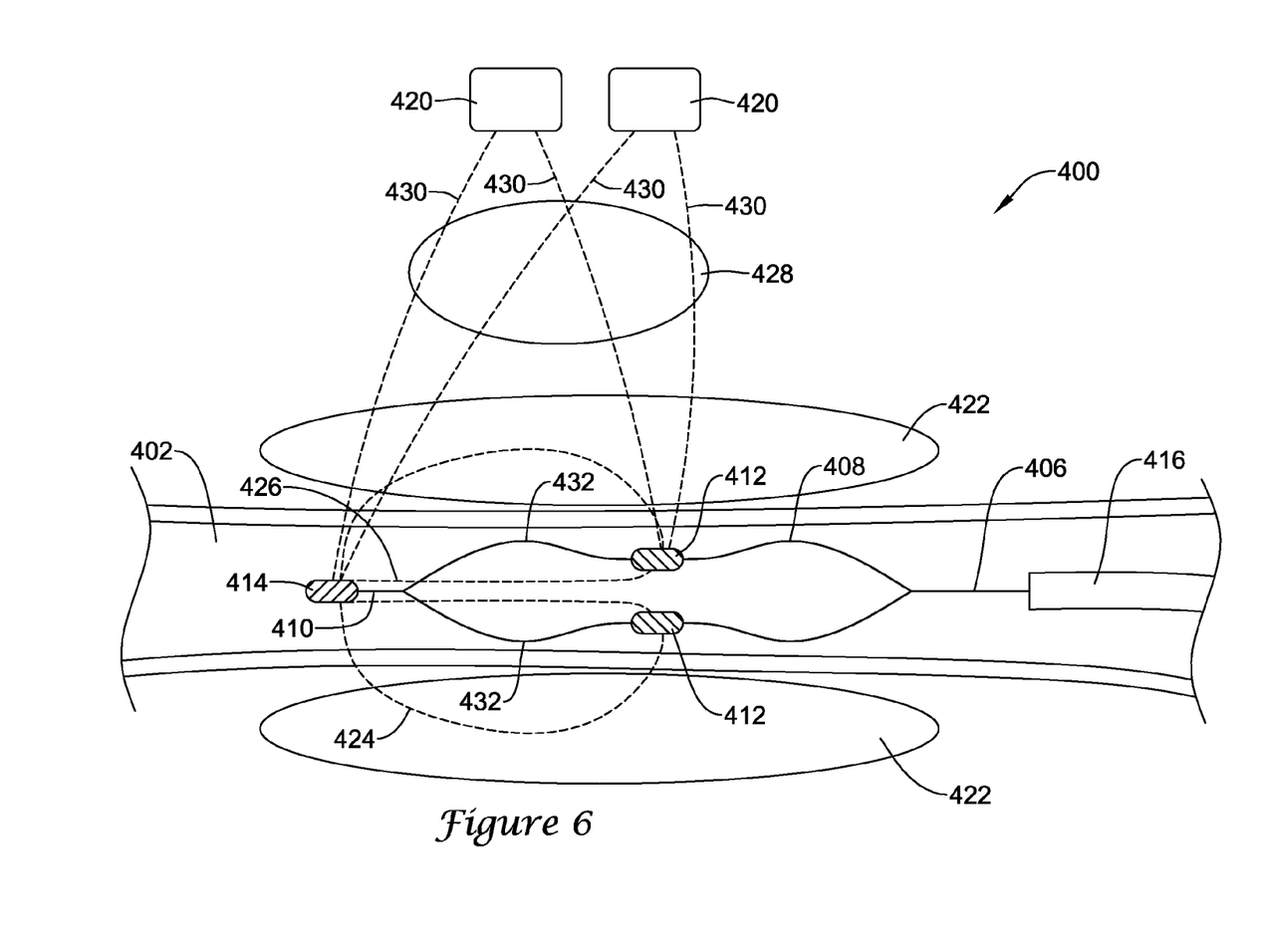
FIG. 6 is another illustrative view of the renal nerve modulation system of FIG. 5.

In some instances, it may be desirable to calculate the impedance of the blood or other fluid within the body lumen 402. The modulation system may include a catheter shaft 416 including a lumen for perfusing saline or other fluid 418 with known conductivity into the body lumen 402. In some instances, the perfused fluid 418 may be provided at room temperature or cooler. It is contemplated that multiple fluids and/or concentrations with known conductivity may be used. The impedance may be determined while the fluid 418 is being perfused. The difference between the impedance calculated with blood and the impedance calculated with the perfused fluid may be used to calculate the impedance of the blood. Referring to FIG. 6, which illustrates the current paths between various electrodes and ground pads, skin-contact ground pads 420 may also be connected through an electrical conductor to the control unit. As voltage is applied to the ablation electrodes 412, current 430 may pass through the local tissue 422 and additional body tissue 428 to the ground pads 420. Analysis of the impedance measurements between the ablation electrodes 412 and the sensing electrode 414 and between the ablation electrodes 412 and the ground pads 420 and/or between the sensing electrode 414 and the ground pads 420 may determine the tissue impedance in the local tissue 422 (e.g. target region) adjacent the electrodes 412, 414.

Tissue impedance may be monitored during simultaneous RF ablation (e.g. energy is applied simultaneously to the ablation electrode 412 and the sensing electrodes 414). In such a case, most of the current 430 may flow between the ablation electrode 412 and the skin-contact ground pads 420 and through the perivascular target tissues to be ablated, while a small amount of current 424, 426 may flow between the ablation electrodes 412 and the sensing electrode 414. As noted above, some of the current 424 will pass through the local tissue 422 while some of the current 426 will pass through the fluid in the body lumen 402 (e.g. blood or perfused fluid). The body impedance resulting from body tissue 428 outside of the local tissue 422 region between the ablation electrode 412 and skin contact ground pad 420 may also be measured. The impedance of the blood, local tissue 422, and body tissue 428 may be used to properly adjust the RF energy applied for ablation of the target tissue. It is further contemplated that impedance of the blood, local tissue 422, and body tissue 428 may be monitored during an ablation/sensing duty cycle which may be used alternate between ablation and impedance measurements. As ablation of the target region progresses, the impedance properties of the local tissue may change thus changing the impedance calculated between the ablation electrode 412 and the contact ground pad 420 and/or between the ablation electrodes 412 and the sensing electrode 414. Multiple measurements between the electrodes 412, 414 and/or the ground pads 420 (with blood or perfused fluid 418) may account for the location of the system 400 and vessel geometry effects. It is contemplated that poor ground pad 420 contact may also be detected during the ablation process.

While not explicitly shown, the ablation electrodes 412 may be connected to a control unit (such as control unit 18 in FIG. 1) by electrical conductors. Once the modulation system 400 has been advanced to the treatment region, energy may be supplied to the ablation electrodes 412. The amount of energy delivered to the ablation electrodes 412 may be determined by the desired treatment as well as the feedback obtained from the impedance calculations. It is contemplated that the impedance of the blood, local tissue 422, and body tissue 428 may be determined prior to and/or during the ablation procedure. Once the target tissue has begun to rise in temperature, and/or denature, the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 400 may monitor impedance values of the surrounding tissue prior to beginning the ablation procedure and adjust the ablation parameters accordingly. It is further contemplated that other electrical properties of the local tissue such as permittivity and/or conductivity may be used to set the current and/or power for RF or other sources of ablation energy to target tissues.

The modulation system 400 may be advanced through the vasculature in any manner known in the art. For example, system 400 may include a guidewire lumen to allow the system 400 to be advanced over a previously located guidewire. In some embodiments, the modulation system 400 may be advanced, or partially advanced, within a guide sheath such as the sheath 16 shown in FIG. 1. Once the ablation electrodes 412 of the modulation system 400 have been placed adjacent to the desired treatment area, positioning mechanisms may be deployed, if so provided. For example, once the distal end region 410 has been placed adjacent to the target region, the catheter shaft 416 may be retracted and the framework 408 allowed to expand. It is contemplated that other known mechanisms may be used to deploy the framework 408. For example, a stent or expandable balloon may be used to expand the framework 408. It is further contemplated that the framework 408 may be formed of a shape-memory material, such as nitinol, such that additional structure is not necessary to expand the framework 408. Expansion of the framework 408 may place the ablation electrodes 412 adjacent to the desired treatment region.

As discussed above, the ablation electrodes 412 and the sensing electrode 414 may be connected to a control unit (such as control unit 18 in FIG. 1) by insulated electrical conductors. Once the modulation system 400 has been advanced to the treatment region, energy may be supplied to the ablation electrodes 412. As discussed above, the energy may be supplied to both the ablation electrodes 412 and/or the sensing electrode 414 simultaneously or in an alternating duty cycle as desired. The amount of energy delivered to the ablation electrodes 412 may be determined by the desired treatment as well as the feedback provided by the sensing electrode 414.

It is contemplated if an ablation electrode 412 is provided that does not extend around the entire circumference of the elongate member 406, the elongate member 406 may need to be circumferentially and/or radially repositioned and energy may once again be delivered to the ablation electrodes 412 to adequately ablate the target tissue. The number of times the elongate member 406 is repositioned at a given longitudinal location may be determined by the number and size of the ablation electrodes 412 on the elongate member 406. Once a particular location has been ablated, it may be desirable to perform further ablation at different longitudinal locations. Once the elongate member 406 has been longitudinally repositioned, energy may once again be delivered to the ablation electrodes 412. If necessary, the elongate member 406 may be radially repositioned at each longitudinal location. This process may be repeated at any number of longitudinal locations desired. It is contemplated that in some embodiments, the system 400 may include ablation electrodes 412 at various positions along the length of the modulation system 400 such that a larger region may be treated without longitudinal displacement of the elongate member 406.

While FIG. 5 illustrates the sensing electrodes 414 in an off-the-wall configuration, it is contemplated that the sensing electrodes 414 may be in direct contact with the vessel wall 404. As the sensing electrodes 414 may be operated at a frequency which does not result in tissue ablation, placing the sensing electrodes 414 against the vessel wall 404 will not cause vessel damage. In instances where direct contact ablation is acceptable, the ablation electrodes 412 may also be placed in contact with the vessel wall 404.

Figure 7:
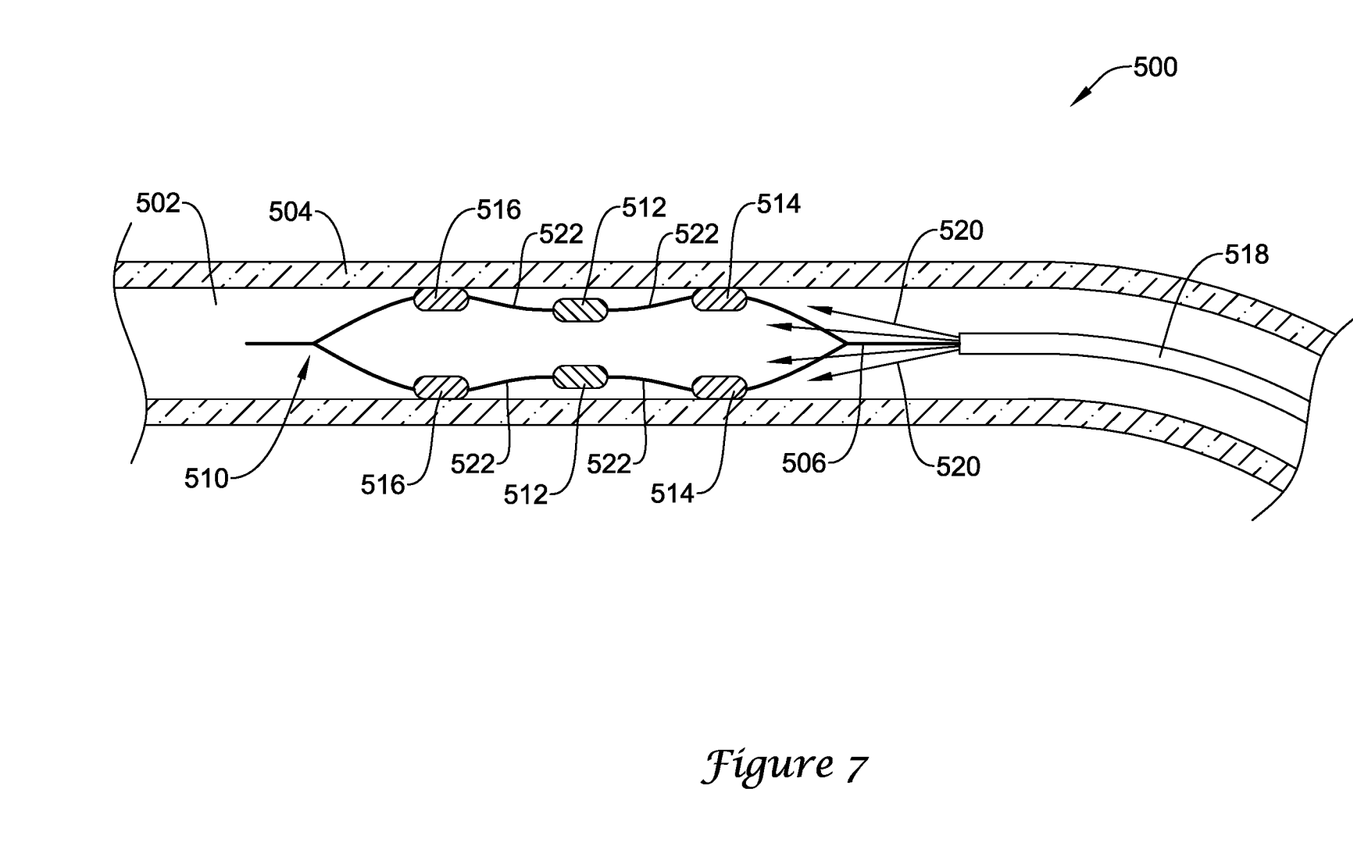
FIG. 7 illustrates a distal end of another illustrative renal nerve modulation system.

FIG. 7 is another illustrative embodiment of a distal end of a renal nerve modulation system 500 that may be similar in form and function to other systems disclosed herein. The modulation system 500 may be disposed within a body lumen 502 having a vessel wall 504. The vessel wall 504 may be surrounded by local target tissue. It may be desirable to determine local tissue impedance and monitor tissue changes in order to control energy delivery for proper target tissue ablation. The nerve modulation system 500 may include one or more high-impedance or low-impedance sensing electrodes 514, 516 to determine local impedance in the target tissue and surrounding blood. It is contemplated that tissue impedance may be monitored during unipolar or bipolar RF, ultrasound, laser, microwave, or other ablation methods.

The system 500 may include an elongate member 506 having an expandable framework 508 disposed adjacent the distal end region 510 may include similar features and may function in a similar manner to the expandable framework described with respect to FIG. 5. The elongate member 506 may extend proximally from the distal end region 510 to a proximal end configured to remain outside of a patient's body. The proximal end of the elongate member 506 may include a hub attached thereto for connecting other treatment devices or providing a port for facilitating other treatments. It is contemplated that the stiffness of the elongate member 506 may be modified to form modulation system 500 for use in various vessel diameters. In some instances, the elongate member 506 may be a wire having a generally solid cross-section. In other embodiments, the elongate member 506 may include one or more lumens extending therethrough. For example, the elongate member 506 may include a guide wire lumen and/or one or more auxiliary lumens. The lumens may be configured in any suitable way such as those ways commonly used for medical devices. While not explicitly shown, the modulation system 500 may further include temperature sensors/wires, an infusion lumen, radiopaque marker bands, fixed guidewire tip, external sheath and/or other components to facilitate the use and advancement of the system 500 within the vasculature.

The system 500 may further include one or more ablation electrodes 512 disposed on the expandable framework 508. The ablation electrodes 512 may be positioned on separate struts 522 of the expandable framework 508 such that the when the framework 508 is expanded the ablation electrodes 512 are positioned adjacent to opposite sides of the vessel wall 504. While the system 500 is illustrated as including two ablation electrodes 512, it is contemplated that the modulation system 500 may include any number of ablation electrodes 512 desired, such as, but not limited to, one, three, four, or more. If multiple ablation electrodes 512 are provided, the ablation electrodes 512 may be longitudinally and/or radially and/or circumferentially spaced as desired. In some instances, the ablation electrodes 512 may be positioned to be adjacent to opposite sides of the vessel 504. The ablation electrodes 512 may include similar features and may function in a similar manner to the ablation electrode discussed with respect to FIG. 2. In some embodiments, the ablation electrodes 512 may be positioned proximal of the distal end region 510 of the elongate member 506. In other embodiments, the ablation electrodes 512 may be positioned adjacent to the distal end region 510. It is further contemplated that the ablation electrodes 512 may function as both ablation and sensing electrodes.

The modulation system 500 may further include a pair of proximal sensing electrodes 514 and a pair of distal sensing electrodes 516. It is contemplated that the modulation system 500 may include fewer than or more than four sensing electrodes 514, 516 to further refine the tissue evaluation. The sensing electrodes 514, 516 may include similar features and may function in a similar manner to the sensing electrodes discussed with respect FIG. 2. In some instances, high-impedance sensing electrodes 514, 516 may be used in order to avoid significant distortion of the electric field and to avoid bipolar ablation between the ablation electrodes 512 and the sensing electrodes 514, 516. In other instances, low-impedance sensing electrodes 514, 516 may be used. The sensing electrodes 514, 516 may be symmetrically placed about the ablation electrodes 512 such that they can easily track the change which occurs to the tissue impedance in the ablation zone located between them. However, the sensing electrodes 514, 516 may be arranged in any orientation desired. The sensing electrodes 514, 516 may be in direct contact with the vessel wall 504. As the sensing electrode 414 may be operated at a frequency which does not result in tissue ablation, placing the sensing electrodes 514, 516 against the vessel wall 504 will not cause vessel damage. In instances where direct contact ablation is acceptable, the ablation electrodes 512 may also be placed in contact with the vessel wall 504. While FIG. 7 illustrates the sensing electrodes 514, 516 in direct contact with the vessel wall, it is contemplated that the sensing electrodes 514, 516 may be positioned away from the vessel wall 504 in an off-the-wall configuration.

The ablation electrodes 512 and the sensing electrodes 514, 516 may be used to monitor the impedance of the local tissue. While not explicitly shown, the ablation electrodes 512 and the sensing electrodes 514, 516 may be connected through separate insulated conductors to a control unit (such as control unit 18 in FIG. 1). The sensing electrodes 514, 516 may be spaced a distance from one another such that voltage applied to the sensing electrodes 514, 516 may cause current to flow between the sensing electrodes 514, 516 through the blood and nearby tissues. Measurement of the current may allow the resistance or complex impedance of the blood and tissue to be calculated. Various frequencies may be used to determine one or more impedance values, or a simpler calculation of resistance at low frequency can be utilized.

In some instances, it may be desirable to calculate the impedance of the blood or other fluid within the body lumen 502. The modulation system may include a catheter shaft 518 including a lumen for perfusing saline 520 or other fluid with known conductivity into the body lumen 502. In some instances, the perfused fluid 520 may be provided at room temperature or cooler. It is contemplated that multiple fluids and/or concentrations with known conductivity may be used. The impedance may be determined while the fluid 520 is being perfused. The difference between the impedance calculated with blood and the impedance calculated with the perfused fluid may be used to calculate the impedance of the blood.

While not explicitly shown, skin-contact ground pads may also be connected through an electrical conductor to the control unit. As voltage is applied to the ablation electrodes 512, current may pass through the local tissue and additional body tissue to the ground pads. Analysis of the impedance measurements between the ablation electrodes 512 and the sensing electrodes 514, 516 and between the ablation electrodes 512 and the ground pads and/or between the sensing electrodes 514, 516 and the ground pads may determine the tissue impedance in the local tissue (e.g. target region) adjacent the electrodes 512, 514, 516.

Tissue impedance may be monitored during simultaneous RF ablation (e.g. energy is applied simultaneously to the ablation electrodes 512 and the sensing electrodes 514, 516) or during an ablation/sensing duty cycle which may be used alternate between ablation and impedance measurements. The tissue impedance may be determined in a similar manner to that discussed with respect to other modulation systems described herein. As ablation of the target region progresses, the impedance properties of the local tissue may change thus changing the impedance calculated between the ablation electrodes 512 and the contact ground pad and/or between the ablation electrodes 512 and the sensing electrodes 514, 516. Multiple measurements between the electrodes 512, 514, 516 and/or the ground pads (with blood or perfused fluid 520) may account for the location of the system 500 and vessel geometry effects. It is contemplated that poor ground pad contact may also be detected during the ablation process.

While not explicitly shown, the ablation electrodes 512 may be connected to a control unit (such as control unit 18 in FIG. 1) by electrical conductors. Once the modulation system 500 has been advanced to the treatment region, energy may be supplied to the ablation electrodes 512. The amount of energy delivered to the ablation electrodes 512 may be determined by the desired treatment as well as the feedback obtained from the impedance calculations. It is contemplated that the impedance of the blood, local tissue, and body tissue may be determined prior to and/or during the ablation procedure. Once the target tissue has begun to rise in temperature, and/or denature, the electrical properties of the tissue may begin to change. As the target tissue is ablated, the change in impedance may be analyzed to determine how much tissue has been ablated. The power level and duration of the ablation may be adjusted accordingly based on the impedance of the tissue. In some instances, the modulation system 500 may monitor impedance values of the surrounding tissue prior to beginning the ablation procedure and adjust the ablation parameters accordingly. It is further contemplated that other electrical properties of the local tissue such as permittivity and/or conductivity may be used to set the current and/or power for RF or other sources of ablation energy to target tissues.

The modulation system 500 may be advanced through the vasculature in any manner known in the art such, but not limited to, those methods discussed with respect to other modulation systems described herein. Once the ablation electrodes 512 of the modulation system 500 have been placed adjacent to the desired treatment area, positioning mechanisms may be deployed, if so provided. For example, once the distal end region 510 has been placed adjacent to the target region, the catheter shaft 518 may be retracted and the framework 508 allowed to expand in similar manners to those discussed with respect to modulation system 400.

As discussed above, the ablation electrodes 512 and the sensing electrodes 514, 516 may be connected to a control unit (such as control unit 18 in FIG. 1) by insulated electrical conductors. Once the modulation system 500 has been advanced to the treatment region, energy may be supplied to the ablation electrodes 512. As discussed above, the energy may be supplied to both the ablation electrodes 512 and/or the sensing electrodes 514, 516 simultaneously or in an alternating duty cycle as desired. The amount of energy delivered to the ablation electrodes 512 may be determined by the desired treatment as well as the feedback provided by the sensing electrodes 514, 516. The modulation system 500 may be radially, longitudinally, and/or circumferentially repositioned and energy subsequently applied as many times as necessary to complete the desired ablation. The number of times the modulation system 500 is repositioned may be determined by the number and size of the ablation electrodes 512 on the elongate member 506.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A nerve modulation system, comprising:
   an elongate shaft having a proximal end region and a distal end region;
   a nerve modulation element disposed adjacent the distal end region; and
   one or more sensing electrodes disposed adjacent to the distal end region;
   wherein the one or more sensing electrodes are configured to monitor impedance of a surrounding region;
   wherein the nerve modulation element is operated at a first frequency; and
   wherein the one or more sensing electrodes are operated at a second frequency different from the first frequency.

2. The system claim 1, wherein the one or more sensing electrodes comprise a first sensing electrode disposed proximal of the nerve modulation element and a second sensing electrode disposed distal of the nerve modulation element.

3. The system of claim 2, wherein the first sensing electrode and the second sensing electrode are positioned symmetrically about the nerve modulation element.

4. The system of claim 1, further comprising a control unit electrically connected to the nerve modulation element and the one or more sensing electrodes.

5. The system of claim 4, wherein the nerve modulation element and the one or more sensing electrodes are electrically connected to the control unit by separate electrical conductors.

6. The system of claim 1, wherein the nerve modulation element is an electrode.

7. The system of claim 1, wherein the nerve modulation element is configured to perform circumferential ablation.

8. The system of claim 1, wherein the second frequency is varied to determine more than one impedance value of a region of tissue.

9. The system of claim 2, wherein current passing between the first and the second sensing electrodes is used to determine an impedance of a region of tissue between the first and the second sensing electrodes.

10. A nerve modulation system, comprising:
a control unit;
an elongate shaft having a proximal end region and a distal end region;
an ablation electrode disposed adjacent the distal end region; and
a first sensing electrode configured to monitor impedance and disposed on the elongate shaft spaced a first distance from the ablation electrode;
wherein the ablation electrode is operated at a first frequency, and wherein the first sensing electrode is operated at a second frequency different from the first frequency.

11. The system of claim 10, wherein the first sensing electrode is configured to measure a voltage of a location in a target region.

12. The system of claim 11, wherein the voltage measured by the first sensing electrode is used to calculate an impedance of a region of tissue between the first sensing electrode and the ablation electrode.

13. The system of claim 10, wherein the second frequency is varied to determine more than one impedance value of a region of tissue.

14. The system of claim 10, further comprising a second sensing electrode configured to monitor impedance and disposed on the elongate shaft spaced a second distance from the ablation electrode, wherein one of the first and second sensing electrodes is positioned proximal of the ablation electrode and another of the first and second sensing electrodes is positioned distal of the ablation electrode.

15. The system of claim 14, wherein current passing between the first and the second sensing electrodes is used to determine an impedance of a region of tissue between the first and the second sensing electrodes.

16. The system of claim 14, wherein the ablation electrode, the first sensing electrode, and the second sensing electrode are electrically connected to the control unit.

17. A nerve modulation system, comprising:
an elongate shaft having a proximal end region and a distal end region;
a nerve modulation element disposed adjacent the distal end region; and
a first sensing electrode disposed on the elongate shaft proximal to the nerve modulation element and a second sensing electrode disposed on the elongate shaft distal to the nerve modulation element;
wherein the nerve modulation element is operated at a first frequency, and wherein the first and second sensing electrodes are operated at a second frequency different from the first frequency.

18. The system of claim 17, wherein the first and second sensing electrodes are configured to monitor impedance of a surrounding region of tissue by passing an impedance sensing current between the first sensing electrode and the second sensing electrode and through the region of tissue.

19. The system of claim 17, wherein the nerve modulation element is configured to perform circumferential ablation.

20. The system of claim 18, wherein the second frequency is varied to determine more than one impedance value of the region of tissue.

* * * * *